United States Patent
Kim et al.

(10) Patent No.: US 12,280,252 B2
(45) Date of Patent: Apr. 22, 2025

(54) ELECTRICAL MUSCLE STIMULATION SYSTEM INCLUDING ELECTRICAL MUSCLE STIMULATION SUIT WEARABLE UNDER WATER

(71) Applicant: COREMOVEMENT CO., LTD., Busan (KR)

(72) Inventors: Myeongcheol Kim, Busan (KR); Seongwoo Je, Busan (KR); Junsul Park, Busan (KR)

(73) Assignee: COREMOVEMENT CO., LTD., Busan (KR)

( * ) Notice: Subject to any disclaimer, the term of this patent is extended or adjusted under 35 U.S.C. 154(b) by 0 days.

(21) Appl. No.: 17/790,142

(22) PCT Filed: Dec. 13, 2021

(86) PCT No.: PCT/KR2021/095121
§ 371 (c)(1),
(2) Date: Jun. 30, 2022

(87) PCT Pub. No.: WO2023/042979
PCT Pub. Date: Mar. 23, 2023

(65) Prior Publication Data
US 2024/0198087 A1    Jun. 20, 2024

(30) Foreign Application Priority Data

Sep. 16, 2021 (KR) .................. 10-2021-0123852
Dec. 1, 2021 (KR) .................. 10-2021-0169705

(51) Int. Cl.
*A61N 1/04* (2006.01)
*A61N 1/36* (2006.01)

(52) U.S. Cl.
CPC ......... *A61N 1/0484* (2013.01); *A61N 1/0452* (2013.01); *A61N 1/36003* (2013.01); *A61N 1/3603* (2017.08)

(58) Field of Classification Search
CPC ............... A61N 1/0484; A61N 1/0452; A61N 1/36003; A61N 1/3603; A61N 1/04; A61N 1/36; A41D 1/00; A41D 7/00
See application file for complete search history.

(56) References Cited

U.S. PATENT DOCUMENTS

| 4,927,041 A | * | 5/1990 | Hepburn | ................ A01K 97/04 |
| | | | | 220/592.25 |
| 9,662,489 B1 | * | 5/2017 | Cargill, III | ......... A61N 1/36014 |

(Continued)

FOREIGN PATENT DOCUMENTS

| JP | 2007-133459 A | 5/2007 |
| JP | 2009-122967 A | 6/2009 |

(Continued)

*Primary Examiner* — Catherine M Voorhees
(74) *Attorney, Agent, or Firm* — Park, Kim & Suh, LLC

(57) ABSTRACT

According to an aspect of the present disclosure, an electrical muscle stimulation system including a control device configured to generate a wireless control signal for controlling an operation of the electrical muscle stimulation suit, may include a buoy module configured to float on a surface of the surface, the electrical muscle stimulation suit may include at least one electrode pad attached to a region corresponding to each muscle part of the user, the buoy module may include a first communication module provided at a position of the buoy module, for transmitting the wireless control signal through air, without passing through water, and wherein the wireless control signal may be transmitted to the electrode pad through wired connection to the electrode pad.

15 Claims, 6 Drawing Sheets

(56) References Cited

U.S. PATENT DOCUMENTS

| | | | | |
|---|---|---|---|---|
| 11,395,919 | B1* | 7/2022 | Pearce | A61N 1/0468 |
| 2005/0187071 | A1* | 8/2005 | Yamashita | A41D 27/00 |
| | | | | 434/247 |
| 2018/0028810 | A1* | 2/2018 | Schwarz | A61N 1/0484 |
| 2021/0069487 | A1* | 3/2021 | Fukae | A61N 1/0452 |

FOREIGN PATENT DOCUMENTS

| | | |
|---|---|---|
| JP | 2013-515529 A | 5/2013 |
| KR | 10-2103052 B1 | 4/2020 |
| WO | 2017/163131 A1 | 9/2017 |

\* cited by examiner

ELECTRICAL MUSCLE STIMULATION SYSTEM INCLUDING ELECTRICAL MUSCLE STIMULATION SUIT WEARABLE UNDER WATER

CROSS-REFERENCE TO RELATED APPLICATIONS

This application is a National Phase Application of PCT International Application No. PCT/KR2021/095121, which was filed on Dec. 13, 2021, and which claims priority from Korean Patent Application No. 10-2021-0123852 filed on Sep. 16, 2021, and Korean Patent Application No. 10-2021-0169705 filed on Dec. 1, 2021. The disclosures of the above patent applications are incorporated herein by reference in their entirety.

TECHNICAL FIELD

The present disclosure relates to an electrical muscle stimulation system in which a buoy module floating on water is connected to an electrical muscle stimulation suit, which is worn by a user under water, to wirelessly make communication with a control device.

BACKGROUND ART

Recently, an electrical muscle stimulation (EMS) device has been attached to a partial surface region of a human body and used to enhance effects of a massage, treatment, an exercise. The EMS may be expected in rapidly enhancing strength of a muscle of a user and rapidly recovering the fatigue of the muscle of the user without requiring an additional exercise or without a burden on a joint due to the exercise, by electrically stimulating muscles adjacent to the attached place to contract the muscles.

DETAILED DESCRIPTION OF THE INVENTION

Technical Problem

An aspect of the present disclosure may provide an electrical muscle stimulation system, capable of transmitting, to an electrical muscle stimulation suit, a wireless control signal of a control device more securely and seamlessly, even if a user is equipped with the electrical muscle stimulation suit under water.

Another aspect of the present disclosure may provide an electrical muscle stimulation system capable of lowering the risk in which the communication module or the power supply unit connected to the electrical muscle stimulation suit is submerged, as the communication module or the power supply unit is positioned outside water, and of more simply exhibiting a waterproof effect, even if the user is equipped with the electrical muscle stimulation suit under water.

Technical Solution

According to an aspect of the present disclosure, an electrical muscle stimulation system may include an electrical muscle stimulation suit to be worn by a user under water, a control device to generate a wireless control signal for controlling an operation of the electrical muscle stimulation suit, and a buoy module to float on a surface of the surface. The electrical muscle stimulation suit may include at least one electrode pad attached to a region corresponding to each muscle part of the user, the buoy module may include a first communication module provided at a position of the buoy module, for transmitting the wireless control signal through air, without passing through water, and the wireless control signal may be transmitted to the electrode pad through wired connection to the electrode pad.

In addition, the electrical muscle stimulation system may further include a waterproof cable connected between the buoy module and the electrical muscle stimulation suit to transmit the wireless control signal from the buoy module to the electrode pad.

In addition, the first communication module may be provided in an upper end region of the buoy module which is not submerged, and the waterproof cable may be connected to a lower region of the buoy module.

In addition, the waterproof cable may be detachable from the electrical muscle stimulation suit.

In addition, the electrical muscle stimulation system may further include a processor. The electric muscle stimulation suit may include a second communication module to receive the wireless con troll signal, and the processor may control the second communication module to receive the wireless control signal through the second communication module, when the waterproof cable is separated.

In addition, the electrical muscle stimulation system may further include a processor, the buoy module may include a first submerging sensor to sense whether the first communication module is submerged, and the processor may include control the first communication module to be turned off, when a submerging sensing signal is received from the first submerging sensor In addition, the electrical muscle stimulation suit may include a second communication module to receive the wireless con troll signal, and a second submerging sensor to sense whether the second communication module is submerged In addition, the processor may control the second communication module to receive the wireless control signal through the second communication module, when receiving the submerging sensing signal from the first submerging sensor, instead of receiving the submerging sensing signal form the second submerging sensor, and control the first communication module to receive the wireless control signal through the first communication module, when receiving the submerging sensing signal from the second submerging sensor, instead of receiving the submerging sensing signal from the first submerging sensor.

In addition, the electrical muscle stimulation suit may include a second communication module to transmit a buoy module connection request signal to the control device, when at least one of the buoy module or the waterproof cable is not electrically connected to the electrical muscle stimulation suit.

In addition, the control device may include a notification unit to notify a buoy module connection request message to a user, when receiving the buoy module connection request signal In addition, the buoy module may include a buoy device provided in the first communication module, and a waterproof case to receive the buoy device, such that the buoy device is sealed from an outside to prevent the buoy device from being submerged.

In addition, the buoy device may include a power supply unit to supply power to the electrical muscle stimulation suit.

In addition, the buoy device may include a first submerging sensor to sense whether the first communication module is submerged.

In addition, the buoy module further may include a floating unit to be detachable from the waterproof case, and the floating unit may be configured such that additional buoyancy is applied to the buoy module in addition to the buoyancy caused by the waterproof case.

Advantageous Effects of the Invention

According to an embodiment of the present disclosure, the wireless control signal of the control device may be transmitted to the electrical muscle stimulation suit more securely and seamlessly, even if the user is equipped with the electrical muscle stimulation suit under water.

According to another aspect of the present disclosure, the risk, in which the communication module or the power supply unit connected to the electrical muscle stimulation suit is submerged, may be lowered, as the communication module or the power supply unit is positioned outside water, and the waterproof effect may be more simply exhibited, even if the user is equipped with the electrical muscle stimulation suit under water.

BEST MODE

Industrial Applicability

Figure 1:
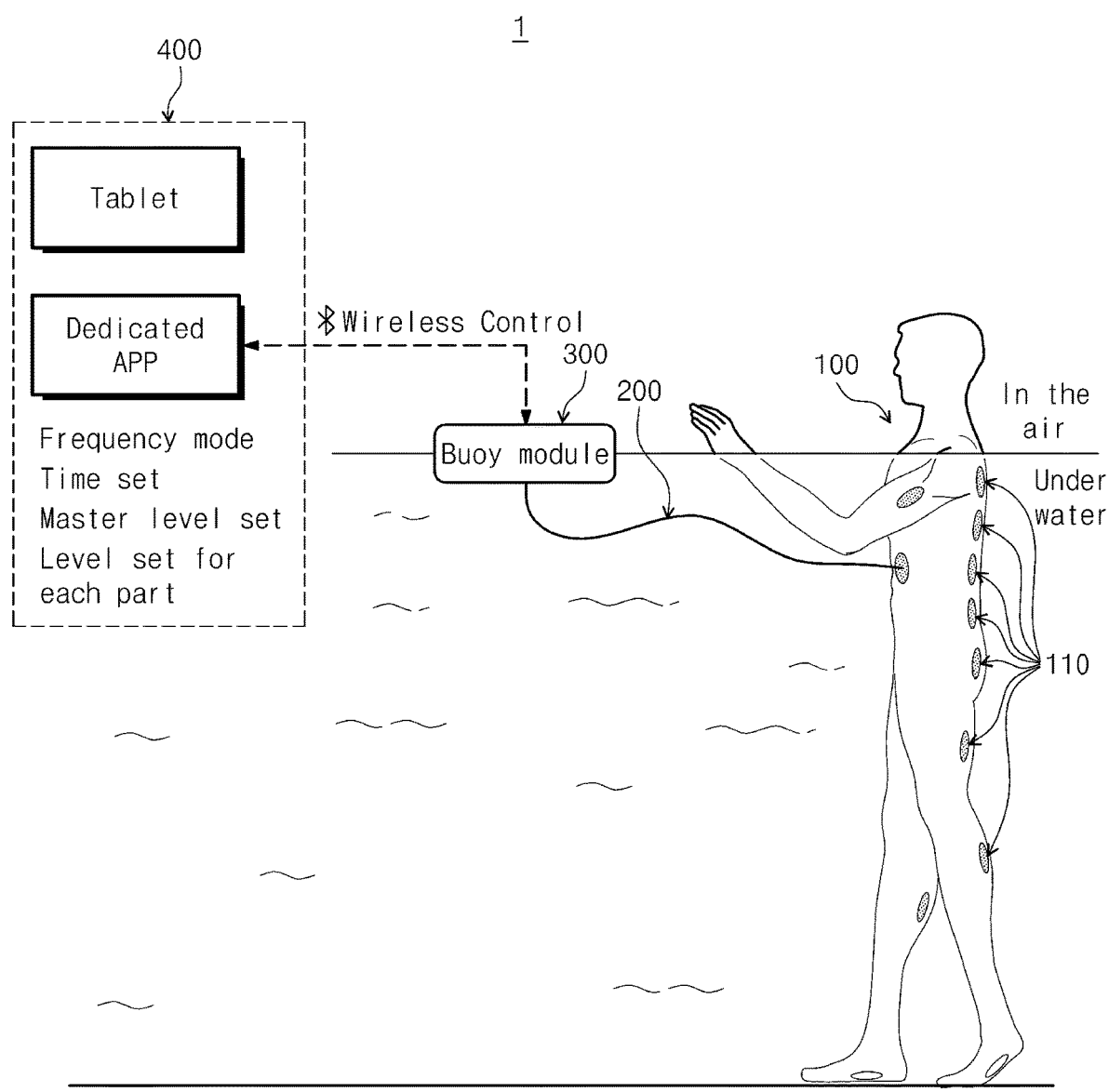
FIG. 1 is a view illustrating an electrical muscle stimulation system, according to an embodiment.

The same reference numerals will be assigned to the same components throughout the whole specification. In the following description of the present specification, all components are not described, and content well known in the art to which the present disclosure pertains or the duplication between embodiments will be omitted. In the specification, the terms "~module", or "~unit" may be implemented in software or hardware. According to embodiments, a plurality of modules and a plurality of parts can be implemented by using one component or one module or one part can include a plurality of components.

It will be understood that the terms "comprises," "comprising," "includes" and/or "including," when used herein, specify the presence of stated elements and/or components, but do not preclude the presence or addition of one or more other elements and/or components.

The term "~module" or "~unit" used herein may refer to software, field programmable gate array (FPGA), or hardware component serving as a unit to perform at least one function or operation. A function provided in the term "~module" or "~unit" may be performed separately in the form of a plurality of components or "~unit", and may be integrated with another additional component. In the specification, the term "~module" or "~unit" may be configured to exist in an addressable storage medium without the limitation to software or hardware or may be configured to operate one or more processors.

In the specification, the term "first and/or second" will be used to distinguish between components, and the components are not limited to the above-described terminology.

The articles "a," "an," and "the" are singular in that they have a single reference, but the use of the singular form in the specification should not preclude the presence of more than one referent.

Reference numerals in steps are only for the illustrative purpose, and not used to describe the sequence of the steps. The steps may be replicated in a sequence different from a sequence, which is described, unless otherwise specified.

Hereinafter, the operating principle and embodiments of the present disclosure will be described with reference to accompanying drawings.

FIG. 1 is a view illustrating an electrical muscle stimulation system according to an embodiment.

Referring to FIG. 1, the electrical muscle stimulation system 1 according to an embodiment of the present disclosure may include an electrical muscle stimulation suit 100, a waterproof cable 200, a buoy module 300, and a control device 400.

In general, an electrical muscle stimulation device is used in a manner to apply appropriate electrical simulation to each muscle of a user, as the user wears a suit-form device in the air.

According to an embodiment of the present disclosure, the user may receive underwater health care or underwater rehabilitation in a manner of electrically stimulating the muscle of the user in the state that the user equipped with the electrical muscle simulation device enters water.

The electrical muscle stimulation suit 100 may be worn by a user under water. Meanwhile, the electrical muscle stimulation suit 100 may be worn and used even in the air outside the water according to a user selection.

The control device 400 may generate a wireless control signal for controlling an operation of the electrical muscle stimulation suit 100.

The communication unit 410 provided in the control device 400 may transmit various wireless control signals to the buoy module 300 and the electrical muscle stimulation suit 100 or receive various wireless control signals through a wireless communication network.

The wireless control signal refers to a wireless signal wireless transmitted and received between various communication modules. For example, the wireless control signal includes, but is not limited to, a Wi-Fi signal, a 3G signal, a 4G signal, or a 5G signal.

The buoy module 300 may be configured to float on the surface of water. For example, the user may naturally float the buoy module 300 on the surface of water such as the pool, as the user wearing the suit enters the swimming pool.

The buoy module 300 may float on water because the density thereof is lower than the density of water used, based on the overall volume.

Figure 2:
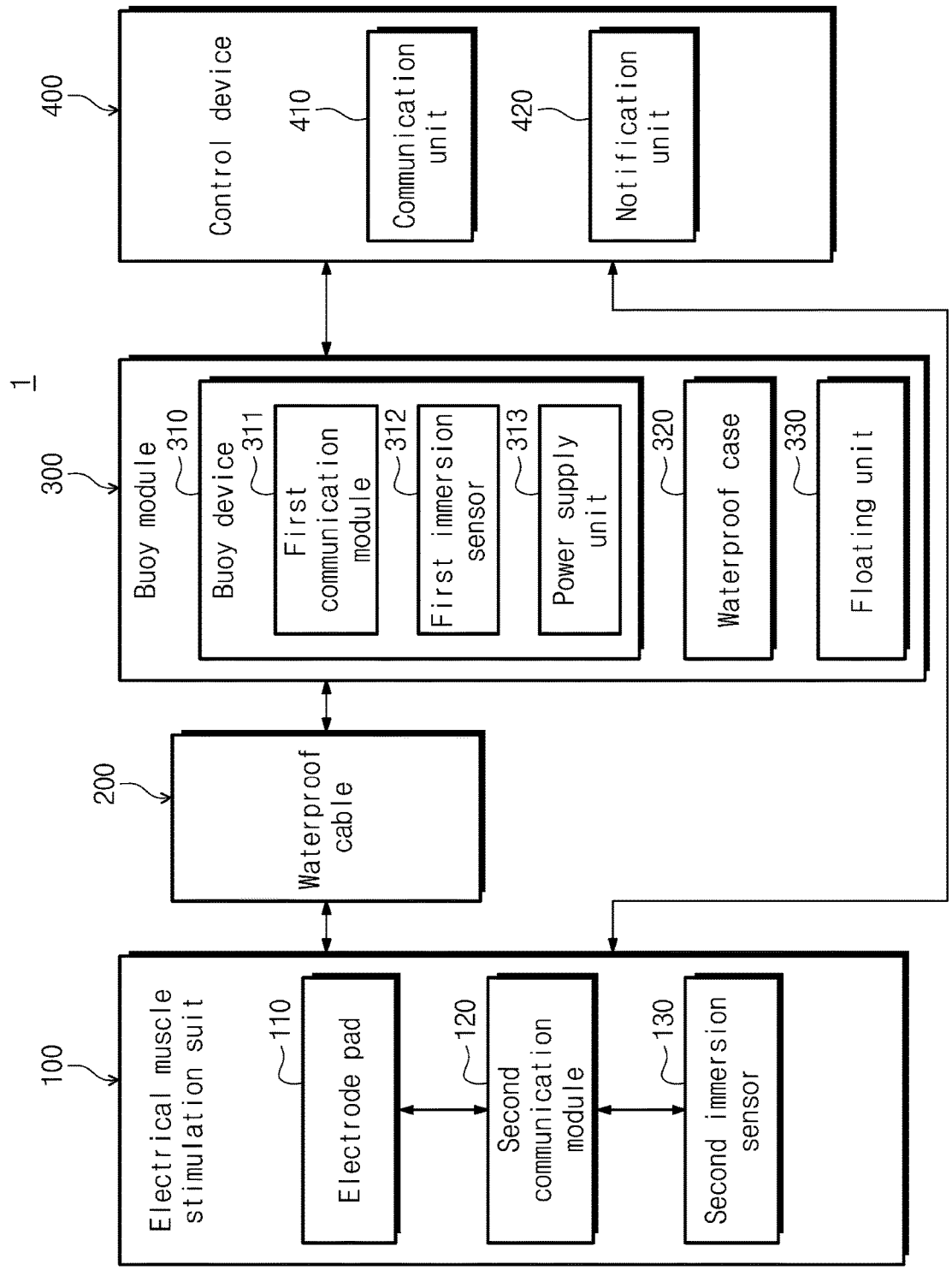
FIG. 2 is a block diagram of an electrical muscle stimulation system, according to an embodiment.

FIG. 2 is a block diagram of an electrical muscle stimulation system according to an embodiment.

Referring to FIG. 2, the electrical muscle stimulation suit 100 may include at least one electrode pad 110 attached to a region corresponding to each muscle part of the user.

The buoy module 300 may include a first communication module 311. The first communication module 311 may be provided at a position of the buoy module 300, for transmitting a wireless control signal through air, without passing through water.

The buoy module 300 may be wired to the electrode pad 110 to transmit the wireless control signal, which is received by the first communication module 311, to the electrode pad 110.

Each electrode pad 110 may provide electrical stimulation to a human body depending on mutually different current intensities or frequencies, based on the wireless control signal.

The control device 400 may separately set a master level and a level for each part. The master level may be a level for controlling the current intensity and frequency of the entire electrode pad 110, and the level for each part may be a level for controlling the current intensity and frequency of each of the electrode pads 110.

The control device 400 may be, but is not limited to, a user terminal in which an electrical muscle stimulation application is installed.

The buoy module 300 may include a buoy device 310, a waterproof case 320, and a floating unit 330.

The buoy device 310 may include the first communication module 311, a first submerging sensor 312, and a power supply unit 313.

The electrical muscle stimulation system 1 may include a waterproof cable 200 connected between the buoy module 300 and the electrical muscle stimulation suit 100 to transmit the wireless control signal from the buoy module 300 to the electrode pad 110.

The waterproof cable 200 may be configured to be detachable from the electrical muscle stimulation suit 100.

The electrical muscle stimulation suit 100 may include a second communication module 120 configured to receive the wireless control signal. The second communication module 120 may transmit the received wireless control signal to the electrode pad 110.

The electrical muscle stimulation system 1 may include a processor. The processor may be provided in any one of the components, such as the electrical muscle stimulation suit 100, the control device 400, and the buoy module 300, of the electrical muscle stimulation system 1, and a plurality of processors may be provided in the electrical muscle stimulation suit 100, the control device 400, and the buoy module 300.

The processor may control the second communication module 120 to receive the wireless control signal through the second communication module 120, when the waterproof cable 200 is separated from one of the electrical muscle stimulation suit 100 or the buoy module 300.

In other words, in the electrical muscle stimulation system 1 of the present disclosure, even if the buoy module 300 or the waterproof cable 200 is not connected to the electrical muscle stimulation suit 100, the second communication module 120 provided in the electrical muscle stimulation suit 100 may receive a wireless control signal to control the electrode pad 110.

The buoy device 310 may include the first submerging sensor 312. The first submerging sensor 312 may sense whether the first communication module 311 is submerged. When the first communication module 311 is submerged, the first submerging sensor 312 may generate a submerging sensing signal and transmit the submerging sensing signal to the processor.

The processor may control the first communication module 311 such that the first communication module 311 is turned off, when the submerging sensing signal is received from the first submerging sensor 312.

The electrical muscle stimulation suit 100 may include a second submerging sensor 130. The second submerging sensor 130 may sense whether the second communication module 120 is submerged.

When the processor receives the submerging sensing signal from the first submerging sensor 312, instead of receiving the submerging sensing signal form the second submerging sensor 130, the processor may control the second communication module 120 to receive a wireless control signal through the second communication module 120.

In addition, when the processor receives the submerging sensing signal from the second submerging sensor 130, instead of receiving the submerging sensing signal from the first submerging sensor 312, the processor may control the first communication module 311 to receive the wireless control signal through the first communication module 311.

In other words, the electrical muscle stimulation system 1 according to the present disclosure may selectively use the communication module of the buoy module 300 or the communication module of the electrical muscle stimulation suit 100, depending on whether an inner part of the buoy module 300 or the electrical muscle stimulation suit 10 is submerged, due to carelessness or damage of the user, such that safe treatment or rehabilitation may be provided to the user.

The second communication module 120 may transmit a buoy module connection request signal to the control device 400, when at least one of the buoy module 300 or the waterproof cable 200 is not electrically connected to the electrical muscle stimulation suit 100.

The control device 400 may include a notification unit 420. The notification unit 420 may be a component which notifies various types of information to a user. The notification unit 420 may notify the information to the user, regardless of any one of a manner of displaying information on a display screen or a manner of outputting a sound through a speaker.

When the control device 400 receives the buoy module connection request signal, the notification unit 420 may notify the buoy module connection request message to user. In this case, the buoy module connection request message may be displayed on a display, or may be output in the form of a sound from a speaker.

The method for controlling the electrical stimulation system according to the embodiment of the present disclosure described until now and an embodiment described to be described may be implemented in the form of a program which may be driven by a processor.

In this case, the program may include program instructions, data files, data structures, etc. independently or may include a combination thereof. The program may be designed and implemented by using machine codes or high-level language codes. The program may be specifically designed to implement a method for correcting the above-described signs or may be implemented by using various functions or definitions which are well known or available to those skilled in a computer software field. The program for implementing the method for indicating the above-described information may be recoded in a recording medium readable by the processor. In this case, the recording medium may be a memory.

The memory may store a program for executing the above-described operation and the operation to be described. The memory is to execute the stored program. When a plurality of processors and a plurality of memories are used, they can be integrated in one chip or can be separately provided at physical positions. The memory may include a volatile memory such as a static random access memory (S-RAM) to temporarily memorize data or a dynamic random access memory (D-RAM). In addition, the memory may include a non-volatile memory, such as a read only memory (ROM), an erasable programmable read only memory (EPROM), an electrically erasable programmable read only (EEPROM) to store a control program and control data in a long term. The processor may include various logic circuits and computing circuits, may process data depending on a program provided from the memory, and may generate a control signal depending on the processing result.

Figure 3:
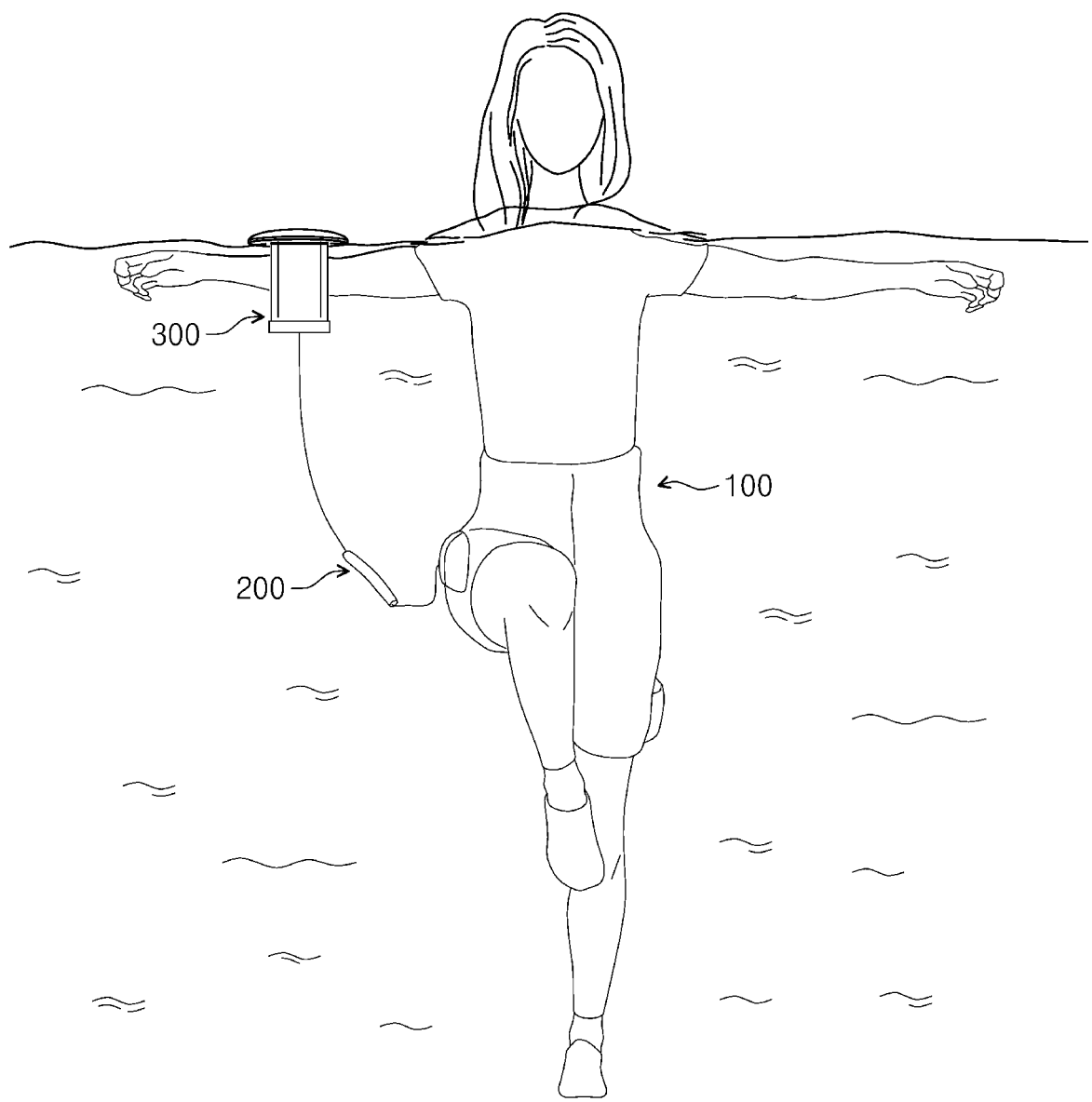
FIG. 3 is a view illustrating a user using an electric muscle stimulation suit and a buoy, according to an embodiment.

FIG. 3 is a view illustrating a user using an electric muscle stimulation suit and a buoy according to an embodiment.

Referring to FIG. 3, a user may receive treatment in a swimming pool while wearing the electrical muscle stimulation suit 100. In this case, when the communication module of the electrical muscle stimulation suit 100 is under the water surface, the control device 400 and the electrical muscle stimulation suit 100 may not smoothly make communication with each other.

In other words, when the communication module, which receives the wireless control signal of the control device 400 and transmits the wireless control signal to the electrical muscle stimulation suit 100, may be positioned on the water surface or be at least close to the water surface, the communication module may smoothly receive the wireless control signal.

Since the first communication module 311 according to an embodiment is provided in the buoy module 300, rather than the electrical muscle stimulation suit 100, the first communication module 311 may be positioned on the water surface.

The signal wirelessly received by the first communication module 311 from the control device 400 may be transmitted to the electrical muscle stimulation suit 100, which is positioned under the water surface, through the waterproof cable 200.

Accordingly, as long as only the buoy module 300 is floating on the water surface, regardless of the user posture in the water or the user position, the electrical muscle stimulation suit 100 may wirelessly receive the control signal.

In other words, the communication module may receive the wireless control signal from the control device 400 without distortion or interruption of the signal. In addition, the risk in which the communication module or the power supply unit 313 is submerged may be lowered.

Figure 4:
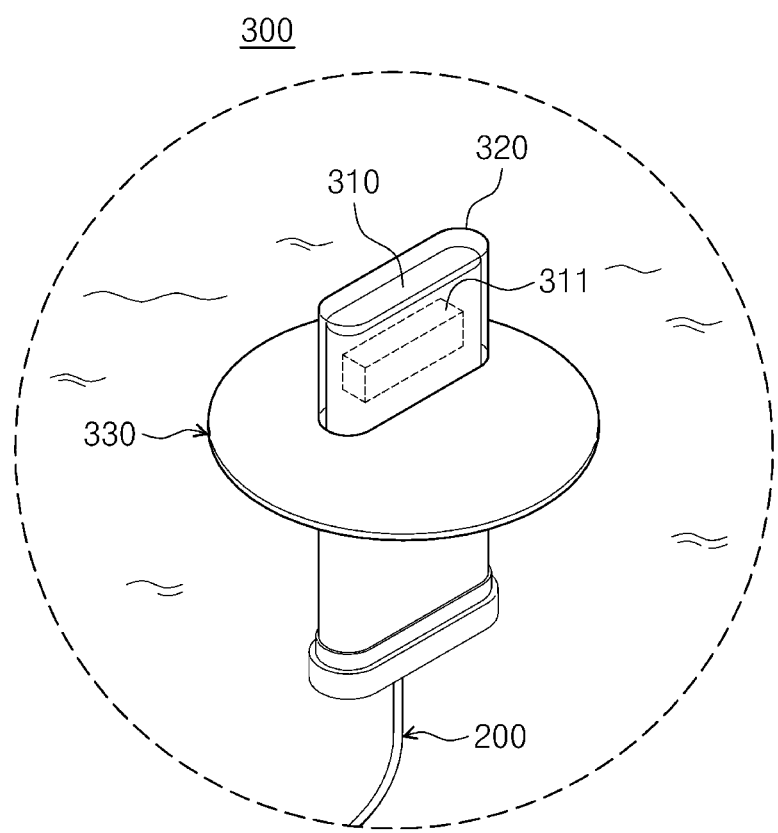
FIG. 4 is a view illustrating a buoy module floating on a water surface, according to an embodiment.

FIG. 4 is a view illustrating a buoy module floating on a water surface according to an embodiment.

Referring to FIG. 4, the buoy module 300 may be configured in a form in which the buoy device 310, the waterproof case 320, and the floating unit 330 are combined.

The first communication module 311 may be provided in an upper end region of the buoy module 300 which is not submerged. Specifically, the first communication module 311 may be provided in a region positioned on the water surface, even in the buoy device 310, when the buoy module 300 is floating under water.

In other words, since the first communication module 311 is provided in a region, which is positioned on the water surface, of the buoy device 310, the first communication module 311 may wirelessly receive a control signal through the air, without worrying about signal distortion or disconnection due to water.

The waterproof cable 200 may be configured to be connected to a lower region of the buoy module 300.

The waterproof cable 200 may be connected to a lower end region of the buoy module 300, to continuously maintain the center of gravity of the buoy module 300 to be stable, such that the buoy module 300 is not overturned.

Accordingly, since the waterproof cable 200 is connected to the lower end region of the buoy module 300, the first communication module 311 of the buoy module 300 may be continuously positioned outside the water to stably receive the wireless control signal.

The floating unit 330 may be configured to be detachable from the waterproof case 320. The floating unit 330 may be configured such that additional buoyancy is applied to the buoy module 300 in addition to the buoyancy caused by the waterproof case 320.

The floating unit 330 may be connected to the outside of the waterproof case 320 to provide additional buoyancy to the buoy module 300. In addition, the floating unit 330 may be configured to stably float on the water surface without being overturned or severely shaken.

Meanwhile, the buoy module 300 according to an embodiment is not necessarily configured in a form in which the buoy device 310, the waterproof case 320, and the floating unit 330 are combined.

For example, as long as the waterproof case 320 including the buoy device 310 may float on the water surface due to the buoyancy of the waterproof case 320, the buoy module 300 may be configured in a form in which the buoy device 310 is provided inside the waterproof case 320 and combined with the waterproof case 320.

Alternatively, as long as the buoy device 310 is waterproofed to prevent from being submerged and floats on the water with the self-buoyancy of the buoy device 310, the buoy module 300 according to an embodiment may include only one buoy device 310.

Figure 5:
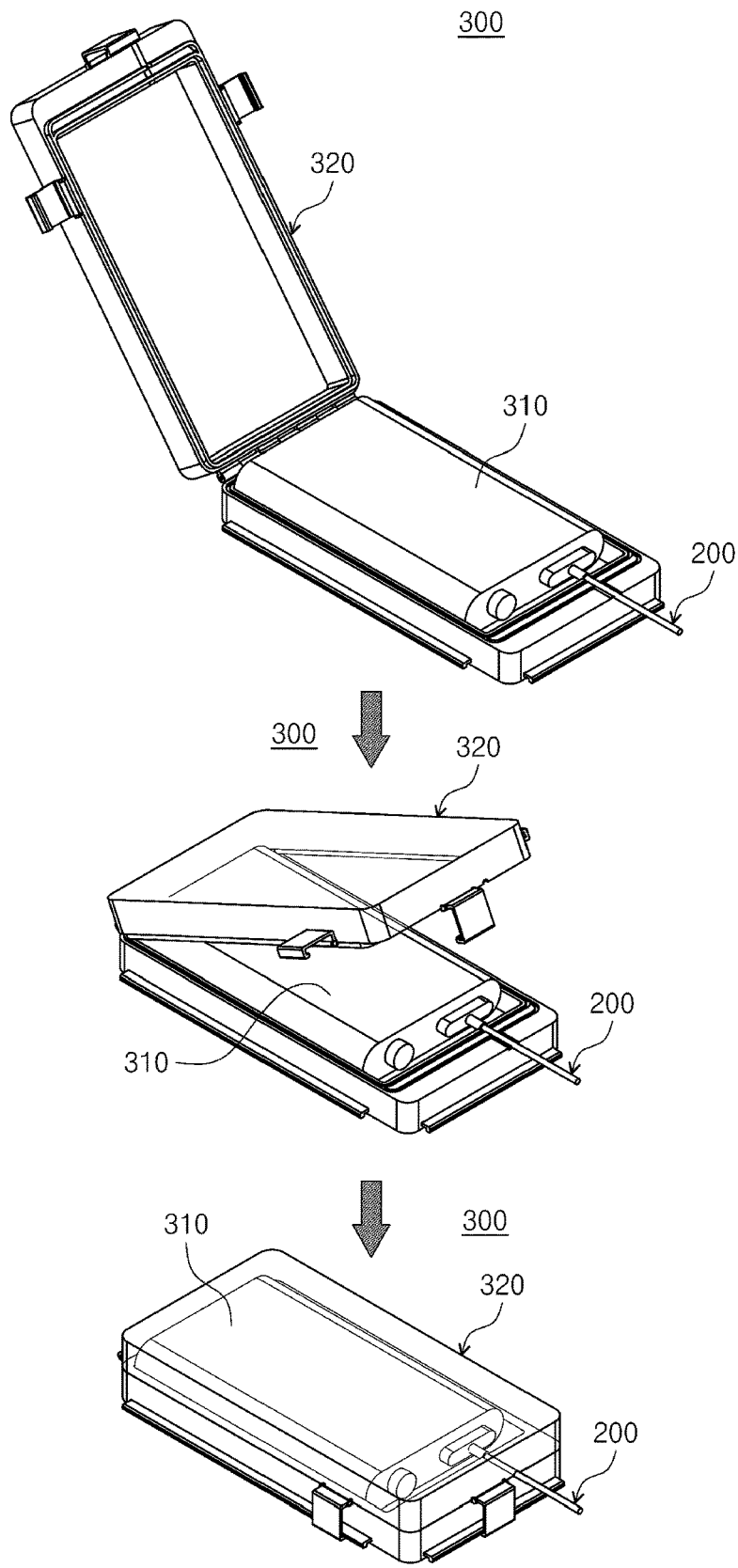
FIG. 5 is a view illustrating a process of assembling a buoy module by combining a buoy device and a waterproof case, according to an embodiment.

FIG. 5 is a view illustrating a process of assembling the buoy module by combining the buoy device and the waterproof case 320 according to an embodiment.

Referring to FIG. 5, the buoy module 300 may be simply assembled by coupling the buoy device 310, such that the buoy device 310 is positioned inside the waterproof case 320.

The waterproof case 320 may receive the buoy device 310 such that the buoy device 310 is sealed from the outside to be prevented from being submerged.

In other words, the buoy device 310 may be provided inside the waterproof case 320, and the waterproof case 320 may be sealed to prevent external water from flowing into the waterproof case 320.

The waterproof case 320 may be formed by coupling two closely contactable components to each other. Accordingly, when the waterproof case 310 is not used, the two components are simply coupled to each other through a hinge. When the waterproof case is used, the two components make close contact with each other, such that the inner part of the waterproof case 320 is sealed from the outside.

In this case, the waterproof cable 200 connected to the buoy device 310 may extend from the inside of the waterproof case 320 to the outside of the waterproof case 320, through a through hole provided in the waterproof case 320. A rubber material may be provided in the contact region between the waterproof cable 200 and the waterproof case 320 to maintain the inside of the waterproof cable 200 to be sealed such that a gap is not formed.

Meanwhile, the shape of the waterproof case 320 is not limited to those illustrated in FIG. 5, and a manner in which the buoy device 310 and the waterproof case 320 are coupled to each other is not limited to those illustrated in FIG. 5.

Figure 6:
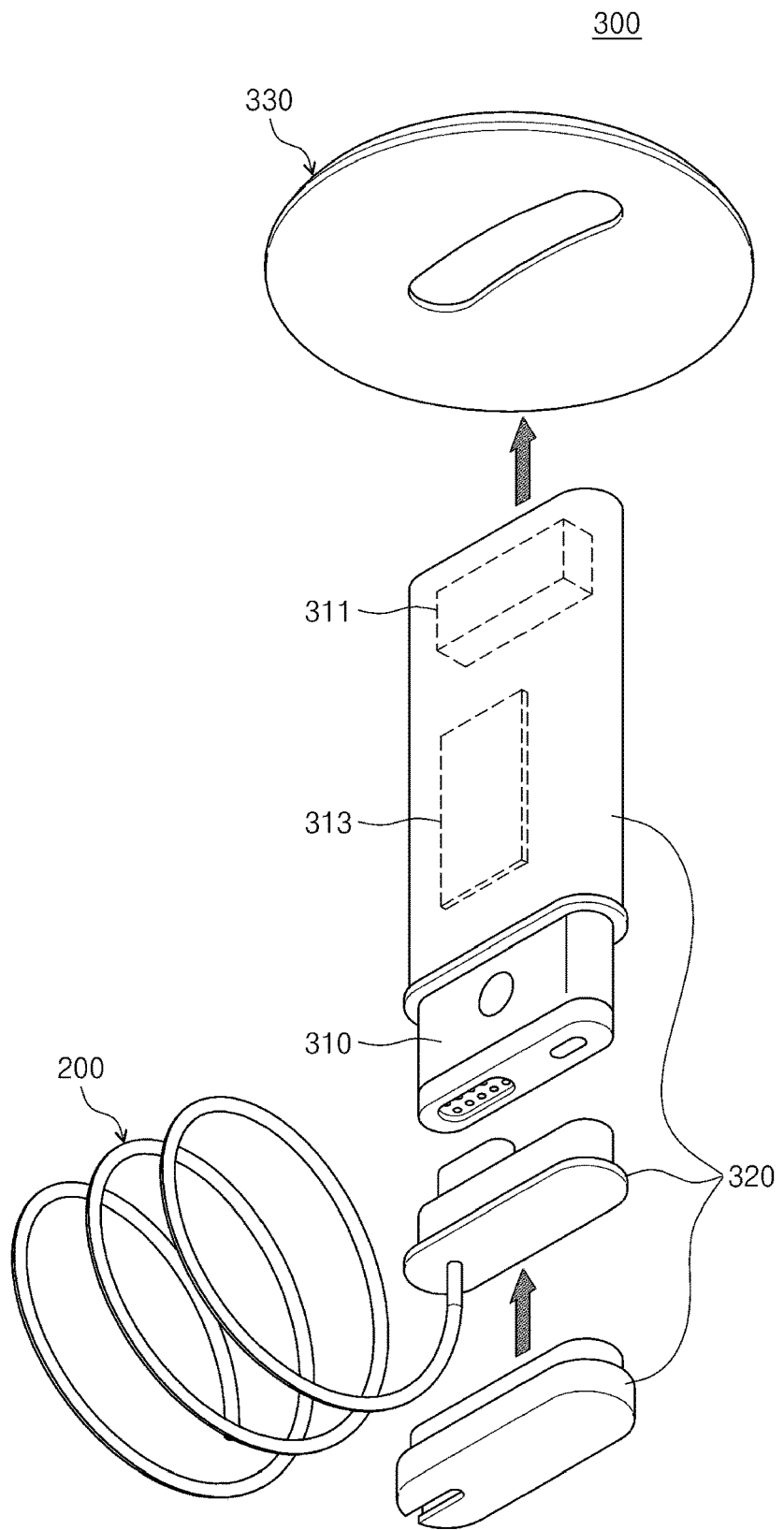
FIG. 6 is a view illustrating a configuration of a buoy module, according to an embodiment.

FIG. 6 is a view illustrating a configuration of a buoy module, according to an embodiment.

Referring to FIG. 6, the waterproof case 320 may be separately divided into two or more components, such as a main body and a lid, when not used, and the inner part of the waterproof case 320 may be sealed from the outside, as the lid is covered on the main body, when used.

In this case, the waterproof cable 200 connected to the buoy device 310 may be connected from the inside of the waterproof case 320 to the outside of the waterproof case 320 through the through the hole provided in the lid. In addition, the end of the waterproof cable 200 connected to the buoy device 310 may be configured as a portion, which functions as a lid, of the waterproof case 320.

The buoy device 310 may include the power supply unit 313 configured to supply power to the electrical muscle stimulation suit 100. The power supply unit 313 may include a large-capacity battery.

The power supply unit 313 is positioned in the buoy device 310 rather than the electrical muscle stimulation suit 100 submerged under water, such that power is more safely supplied to the electrode pad 110.

The waterproof case 320 having the buoy device 310 mounted therein and covered and sealed with the lid may be coupled to the floating unit 330.

In this case, although the waterproof case 320 may be coupled to the floating unit 330, as an outer surface of the waterproof case 320 is merely fitted into a through hole provided in the floating unit 330, the coupling scheme between the waterproof case 320 and the floating unit 330 is not limited thereto. In other words, as long as the floating unit 330 is configured to apply additional buoyancy to the buoy module 300 in addition to the buoyancy caused by the waterproof case 320, the waterproof case 320 and the floating unit 330 may be coupled to each other through various coupling schemes.

In other words, the buoy module 300 according to an embodiment is not one single detachable device. In other words, the buoy module 300 is basically divided into the buoy device 310, the waterproof case 320, and the floating unit 330. When the user intends to use the electrical muscle stimulation suit 100, the user may put the buoy device 310 into the waterproof case 320, may close and seal the lid of the waterproof case 320, may mount the floating unit 330 in the waterproof case 320, thereby simply manufacturing the buoy module 300.

To the contrast, when the user intends to use the electrical muscle stimulation suit 100 outside the water, the user may dismantle the buoy module 300 such that the buoy device 310 is separated from the waterproof case 320 and the floating unit 330, and may use the buoy device 310 only.

At least one component may be added or deleted to correspond to the performance of the components described above. Furthermore, it will be easily understood by a person with ordinary skill in the art to which the present disclosure pertains that the mutual positions of components may be changed to correspond to the performance or structure of the system.

As described above, the disclosed embodiments have been described with reference to the accompanying drawings. A person with ordinary skill in the art to which the present disclosure pertains will understand which the present disclosure may be implemented in a form different from the disclosed embodiments without changing the technical spirit or essential features of the present disclosure. The disclosed embodiments are exemplary and should not be construed limitedly.

The invention claimed is:

1. An electrical muscle stimulation system comprising:
an electrical muscle stimulation suit configured to be worn by a user under water;
a control device configured to generate a wireless control signal for controlling an operation of the electrical muscle stimulation suit; and
a floating device configured to float on a surface of the water,
wherein the electrical muscle stimulation suit includes:
at least one electrode pad adapted to be attached to a region corresponding to a muscle part of the user,
wherein the floating device includes:
a first communication module provided at a position of the floating device, for receiving the wireless control signal through air;
a buoy device in which the first communication module is provided; and
a waterproof case to receive the buoy device so that the buoy device is sealed from an outside to prevent the buoy device from being submerged,
wherein the buoy device includes a first submerging sensor to sense whether the first communication module is submerged, and
wherein the wireless control signal is transmitted to the electrode pad through a wired connection from the floating device.

2. The electrical muscle stimulation system of claim 1, further comprising:
a waterproof cable connected between the floating device and the electrical muscle stimulation suit to transmit the wireless control signal from the floating device to the electrode pad.

3. The electrical muscle stimulation system of claim 2, wherein the first communication module is provided in an upper end region of the floating device which is not submerged, and
wherein the waterproof cable is configured to be connected to a lower region of the floating device.

4. The electrical muscle stimulation system of claim 2, wherein the waterproof cable is configured to be detachable from the electrical muscle stimulation suit.

5. The electrical muscle stimulation system of claim 4, further comprising:
a processor,
wherein the electrical muscle stimulation suit includes:
a second communication module configured to receive the wireless control signal from the control device, and
wherein the processor is configured to:
control the second communication module to receive the wireless control signal from the control device, when the waterproof cable is separated from the floating device or the electrical muscle stimulation suit.

6. The electrical muscle stimulation system of claim 4, further comprising:
a processor,
wherein the floating device includes:
a first submerging sensor configured to sense whether the first communication module is submerged, and
wherein the processor is configured to:

control the first communication module to be turned off, when a submerging sensing signal is received from the first submerging sensor.

7. The electrical muscle stimulation system of claim 6, wherein the electrical muscle stimulation suit includes:
a second communication module configured to receive the wireless control signal from the control device; and
a second submerging sensor configured to sense whether the second communication module is submerged.

8. The electrical muscle stimulation system of claim 7, wherein the processor is configured to:
control the second communication module to receive the wireless control signal from the control device, when receiving the submerging sensing signal from the first submerging sensor; and
control the first communication module to receive the wireless control signal from the control device, when receiving the submerging sensing signal from the second submerging sensor.

9. The electrical muscle stimulation system of claim 1, wherein the electrical muscle stimulation suit includes:
a second communication module to transmit a connection request signal to the control device, when at least one of the floating device or the waterproof cable is not electrically connected to the electrical muscle stimulation suit.

10. The electrical muscle stimulation system of claim 9, wherein the control device includes:
a notification unit configured to notify the user, when receiving the connection request signal from the second communication module.

11. The electrical muscle stimulation system of claim 1, wherein the buoy device further includes:
a power supply unit configured to supply power to the electrical muscle stimulation suit.

12. The electrical muscle stimulation system of claim 1, wherein the floating device further includes:
a floating unit configured to be detachable from the waterproof case, and
wherein the floating unit is configured so that additional buoyancy is applied to the floating device in addition to the buoyancy caused by the waterproof case.

13. The electrical muscle stimulation system of claim 3, wherein the waterproof cable is configured to be detachable from the electrical muscle stimulation suit,
wherein the electrical muscle stimulation suit includes:
a second communication module configured to receive the wireless control signal from the control device; and
a second submerging sensor configured to sense whether the second communication module is submerged,
wherein the second communication module transmits a connection request signal to the control device, when at least one of the floating device or the waterproof cable is not electrically connected to the electrical muscle stimulation suit,
wherein the floating device includes:
a buoy device;
a waterproof case to receive the buoy device so that the buoy device is sealed from an outside to be prevented from being submerged; and
a floating unit configured to apply additional buoyancy to the floating device in addition to the buoyancy caused by the waterproof case,
wherein the buoy device includes:
a processor;
the first communication module;
a power supply unit configured to supply power to the electrical muscle stimulation suit; and
a first submerging sensor configured to sense whether the first communication module is submerged, and
wherein the processor is configured to:
control the second communication module to receive the wireless control signal from the control device, when the waterproof cable is separated from the floating device or the electrical muscle stimulation suit,
control the second communication module to receive the wireless control signal from the control device, when receiving the submerging sensing signal from the first submerging sensor, and
control the first communication module to receive the wireless control signal from the control device, when receiving the submerging sensing signal from the second submerging sensor.

14. An electrical muscle stimulation system comprising:
an electrical muscle stimulation suit configured to be worn by a user under water;
a control device configured to generate a wireless control signal for controlling an operation of the electrical muscle stimulation suit; and
a floating device configured to float on a surface of the water,
wherein the electrical muscle stimulation suit includes:
at least one electrode pad adapted to be attached to a region corresponding to a muscle part of the user,
wherein the floating device includes:
a first communication module provided at a position of the floating device for receiving the wireless control signal through air,
wherein the wireless control signal is transmitted to the electrode pad through a wired connection from the floating device,
wherein the electrical muscle stimulation system further comprises a waterproof cable connected between the floating device and the electrical muscle stimulation suit to transmit the wireless control signal from the floating device to the electrode pad,
wherein the waterproof cable is configured to be detachable from the electrical muscle stimulation suit,
wherein the electrical muscle stimulation system further comprises a processor,
wherein the floating device further includes a first submerging sensor configured to sense whether the first communication module is submerged,
wherein the processor is configured to control the first communication module to be turned off when a submerging sensing signal is received from the first submerging sensor.

15. An electrical muscle stimulation system comprising:
an electrical muscle stimulation suit configured to be worn by a user under water;
a control device configured to generate a wireless control signal for controlling an operation of the electrical muscle stimulation suit; and
a floating device configured to float on a surface of the water,
wherein the electrical muscle stimulation suit includes:
at least one electrode pad adapted to be attached to a region corresponding to a muscle part of the user,
wherein the floating device includes:

a first communication module provided at a position of the floating device for receiving the wireless control signal through air, wherein the wireless control signal is transmitted to the electrode pad through a wired connection from the floating device, wherein the electrical muscle stimulation system further comprises a waterproof cable connected between the floating device and the electrical muscle stimulation suit to transmit the wireless control signal from the floating device to the electrode pad, wherein the first communication module is provided in an upper end region of the floating device which is not submerged, wherein the waterproof cable is configured to be connected to a lower region of the floating device, wherein the waterproof cable is configured to be detachable from the electrical muscle stimulation suit, wherein the electrical muscle stimulation suit includes:
  a second communication module configured to receive the wireless control signal from the control device; and
  a second submerging sensor configured to sense whether the second communication module is submerged, wherein the second communication module transmits a connection request signal to the control device, when at least one of the floating device or the waterproof cable is not electrically connected to the electrical muscle stimulation suit, wherein the floating device includes:
  a buoy device;
  a waterproof case to receive the buoy device so that the buoy device is sealed from an outside to be prevented from being submerged; and
  a floating unit configured to apply additional buoyancy to the floating device in addition to the buoyancy caused by the waterproof case, wherein the buoy device includes:
  a processor;
  the first communication module;
  a power supply unit configured to supply power to the electrical muscle stimulation suit; and
  a first submerging sensor configured to sense whether the first communication module is submerged, wherein the processor is configured to:
  control the second communication module to receive the wireless control signal from the control device, when the waterproof cable is separated from the floating device or the electrical muscle stimulation suit,
  control the second communication module to receive the wireless control signal from the control device, when receiving the submerging sensing signal from the first submerging sensor, and
  control the first communication module to receive the wireless control signal from the control device, when receiving the submerging sensing signal from the second submerging sensor.

* * * * *